United States Patent [19]

Postle et al.

[11] 4,410,702
[45] Oct. 18, 1983

[54] HYDROQUINONE DERIVATIVES OF PYRIDINECARBOXYLIC ACIDS

[75] Inventors: Stephen R. Postle, Brentwood; Patrick D. P. Thomas, Chelmsford, both of England

[73] Assignee: Ciba-Geigy AG, Basel, Switzerland

[21] Appl. No.: 306,847

[22] Filed: Sep. 29, 1981

[30] Foreign Application Priority Data

Oct. 2, 1980 [GB] United Kingdom ............... 8031835

[51] Int. Cl.$^3$ ............................................. C07D 213/55
[52] U.S. Cl. ................................... 546/322; 546/326; 548/484; 549/71
[58] Field of Search ............................ 546/326, 322

[56] References Cited

FOREIGN PATENT DOCUMENTS

| 1258924 | 5/1979 | United Kingdom | 430/405 |
| 2007857 | 5/1979 | United Kingdom | 430/255 |
| 2007862 | 5/1979 | United Kingdom | 430/216 |

OTHER PUBLICATIONS

Bhavsar et al., Chem. Abstracts, vol. 87(19), 151, 978x, Nov. 7, 1977.

*Primary Examiner*—Alan L. Rotman
*Attorney, Agent, or Firm*—Joseph G. Kolodny

[57] ABSTRACT

Compounds of the formula

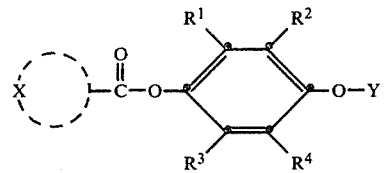

wherein $R^1$, $R^2$, $R^3$ and $R^4$ are hydrogen or alkyl, X represents the atoms to complete an aromatic heterocyclic ring system and Y is hydrogen or has the meaning assigned to X, are readily cleaved in alkaline solutions to release a hydroquinone derivative.

The compounds can be incorporated into photographic materials used for activation processing.

5 Claims, No Drawings

HYDROQUINONE DERIVATIVES OF PYRIDINECARBOXYLIC ACIDS

The present invention relates to novel substituted hydroquinone derivatives and to their use in photographic material.

Hydroquinone is the most widely used developing agent for developing latent silver images in silver halide photographic material. Most usually exposed photographic material is processed in a bath containing hydroquinone to develop the latent image but for some types of processing it is preferable that the hydroquinone is present already in the photographic material which after exposure is processed in an alkaline bath to develop the latent image as hydroquinone only as a developing agent under alkaline conditions. Such a method of processing is known as activation processing. Activation processing is extremely rapid but it is not widely employed except in certain special circumstances because the disadvantages of incorporating hydroquinone in the photographic material outweigh the advantages. These disadvantages include developer decomposition on ageing and interference with the setting and hardening of the gelatin or other colloidal layers in which it is incorporated during the coating of the photographic material. Further, activation processing often tends to cause stain and tanning of the processed material.

In an effort to overcome these disadvantages it has been proposed to use protected hydroquinones which are substituted hydroquinones in which the protecting group or groups are cleaved at the high pH-value of the alkaline processing bath. However it has proved difficult to find substituted hydroquinones which are readily cleavable in the alkaline bath and thus which release the active hydroquinone quickly enough to achieve rapid processing and also substituted hydroquinones which are stable during coating and on storage of the photographic material. Many of the proposed substituted hydroquinone compounds contain in the protective moiety desensitising groups which limit the use of such compounds or are coloured due to the presence of chromophoric groups, such as nitro groups, in the protective moiety. Such coloured compounds may be of use in certain circumstances but their presence tends to cause speed losses in the photographic material.

Of the proposed substituted hydroquinones for use in photographic material some are water-soluble compounds as described for example in GB No. 1 258 924 and some are water-insoluble compounds as described for example in Research Disclosure 16444 of December 1977.

It has now been found a novel class of substituted hydroquinone compounds which cleave rapidly in alkaline solution and exhibit superior storage stability and little tendency to cause stain or tanning problems when material which contains them is activation processed. None of these compounds which may be water-soluble or water-insoluble is coloured and most do not contain any desensitising groups.

According to the present invention there is provided a substituted hydroquinone compound of the formula

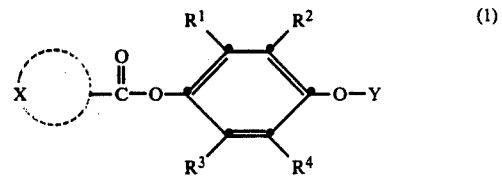

wherein $R^1$, $R^2$, $R^3$ and $R^4$ are each hydrogen or alkyl having from 1 to 4 carbon atoms, X represents the atoms necessary to complete an aromatic heterocyclic ring system which is optionally quaternised with alkyl or aralkyl containing from 1 to 7 carbon atoms if the heterocyclic ring is pyridinyl or one of its benzannellated derivatives and Y is hydrogen or a group of the formula

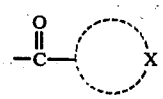

wherein X is as defined above.

Preferably,

is attached to the hetercyclic ring through a carbon atom.

Another object of the present invention relates to a method for the manufacture of the compounds of formula (1).

According to another aspect of the present invention there is provided photographic silver halide material which comprises on a support at least one colloid silver halide layer and at least one colloid layer which comprises at leat one substituted hydroquinone compound of formula (1).

Another object of the present invention is a process for the manufacture of this photographic material.

In the compounds of formula (1), $R^1$, $R^2$, $R^3$ and $R^4$ are each hydrogen or alkyl having 1 to 4 carbon atoms such as methyl, ethyl, propyl, i-propyl, butyl or t-butyl. Methyl and t-butyl are preferred. More preferably, $R^1$, $R^2$, $R^3$ and $R^4$ are hydrogen.

X denotes the atoms which are necessary to complete an aromatic heterocyclic ring system. Preferably, these ring systems contain 5 or 6 ring atoms, at least one atoms being a carbon atom, the heteroatom(s) being oxygen, sulphur and/or preferably nitrogen. These rings re optionally substituted or quaternised if the heterocycle contains a nitrogen atom and they may be benzannellated. Examples of ring systems are furanyl, thiophenyl, pyrrolyl and benzannellated derivatives thereof. However, monocyclic aromatic ring systems are preferred. More suitable radicals X are represented by pyridyl radicals such as 2-, 3- or 4-pyridyl or benzannellated derivatives thereof. As mentioned above the nitrogen containing rings are optionally substituted or quaternised by alkyl or aralkyl having from 1 to 7 carbon atoms. Examples of suitable alkyl and aralkyl residues are methyl, ethyl, propyl, butyl, pentyl, hexyl, heptyl and isomers thereof, further benzyl and phenyl ethyl. Methyl, ethyl and benzyl are preferred. Especially preferred is methyl.

Y has the meaning assigned to X. Preferably, Y is hydrogen.

Compounds of formula (1) may be prepared—and this is another object of the present invention—by reacting an acid chloride of the formula

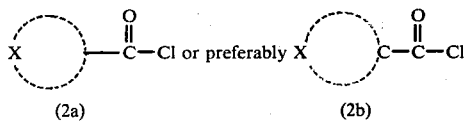

where X has the meaning assigned to it above with a hydroquinone of the formula

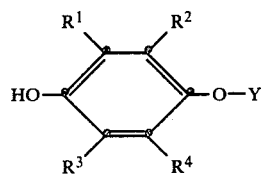

wherein $R^1$, $R^2$, $R^3$, $R^4$ and Y have the meanings assigned to them above in the presence of an organic solvent and a base.

Suitable solvents include e.g. acetone, acetonitrile and methylene chloride.

Suitable bases include e.g. pyridine and triethylamine.

Alternatively the compounds of formula (1) may be prepared using a Schotten-Baumann reaction wherein the hydroquinone compound of formula (3) dissolved in aqueous sodium carbonate solution is reacted with the acid chloride of formula (2) in an aqueous medium.

This latter reaction procedure may be employed even when the acid chloride of formula (2) is water-insoluble.

Usually silver halide photographic material which is to be activation processed comprises only one silver halide colloid layer and most usually this colloid is gelatin.

Therefore according to a preferred embodiment of this aspect of the present invention there is provided photographic silver halide material which comprises coated on a support at least one colloid layer which comprises at least one substituted hydroquinone of formula (1). Preferably, the photographic silver halide material comprises on a support a gelatine silver halide emulsion layer which comprises a substituted hydroquinone of formula (1).

The amount of the compound of formula (1) present in the silver halide photographic material will depend on the actual compound used and on the proposed use of the photographic material. Preferably however the compound of formula (1) is present in the photographic material in an amount within the range of 0.1 to 1.0 moles per 1.5 moles of silver halide present in the photographic material.

Preferably the substituted hydroquinones of formula (1) which are water-insoluble are dispersed in the layer of the photographic material as a solid dispersion which has been obtained by ball-milling the solid in an aqueous medium in the presence of a wetting agent. Alternatively the water-insoluble compounds of formula (1) may be dispersed in the layer of the photographic material in an oil, for example tricresyl phosphate.

The silver halide present in the photographic material may be any one of the normally employed silver halides such as silver chloride, silver bromide, silver chlorobromide, silver bromoiodide and silver iodochlorobromide.

The silver halide emulsions may be optically sensitised by the presence therein of optical sensitising dyes, for example merocyanine or carbocyanine dyes.

The silver halide emulsions may contain any of the additives commonly used in photographic emulsions, for example wetting agents such as polyalkylene oxides, stabilising agents such as tetra-azaindenes, metal sequestering agents and growth or crystal habit modifying agents commonly used for silver halide such as adenine.

Preferably the colloid medium is gelatin or a mixture of gelatin and a water-soluble latex, for example a latex vinyl acrylate-containing polymer. Most preferably if such a latex is present in the final emulsion it is added after all crystal growth has occurred. However, other water-soluble colloids, for example casein, polyvinylpyrrolidone or polyvinyl alcohol, may be used alone or together with gelatin.

The support may be any one of the supports normally used for photographic materials including paper base, polyethylene-coated paper base, oriented and subbed polyethylene terephthalate, cellulose triacetate, cellulose acetate butyrate, polystyrene and polycarbonate.

The photographic material of the present invention may be used in a large number of different ways including black and white print material, X-ray film material, colour film material, microfilm products and direct positive material.

The photographic material of the present invention most usually is prepared by forming an aqueous colloid coating solution of the silver halide which comprises either a dispersion of the compound or formula (1) or a solution of the compound of formula (1) and this colloid coating solution is coated as a layer on a support and dried.

After exposure the photographic material may be treated with an activator solution which is an aqueous alkaline solution which comprises for example sodium hydroxide or sodium carbonate. Most usually the activator solution will have a pH-value of between 10 and 14. Stabilisers, antifoggants and development accelerators may also be present in the activator solutions.

The activator solutions may be applied to the exposed photographic material according to the present invention in all the usual ways such as surface application, total immersion of the material in the activator solution and spraying.

After the inventive photographic material has been activator processed it may be fixed in a silver halide fixing solution, for example ammonium thiosulphate, to remove the undeveloped silver halide, or it may be stabilised to render the remaining silver halide lightsensitive by treatment with a known stabiliser treatment solution, for example an aqueous ammonium thiocyanate solution.

The following Examples will serve to illustrate the invention.

EXAMPLE I

Preparation of the compound of the formula

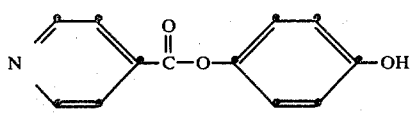 (C)

Isonicotinoyl chloride (17.4 g), hydroquinone (11 g) and and acetonitrile (100 ml) are stirred at ambient temperature. Pyridine (10 ml) is added dropwise and stirring continued further 90 minutes. The mixture is poured into water and the precipitated ester filtered, washed with water and dried. Recrystallisation from methanol/water affords a white solid (9.1 g), m.p. 175°–177° C.

Compounds (A), (B), (D) and (E) are prepared similarly using the appropriate acid chloride.

EXAMPLE II

Preparation of the compound of the formula (G)

Compound (G) is prepared from compound (C) by taking 1.08 g of compound (C) as just prepared and dimethyl sulphate (0.63 g). These compounds are heated under reflux in xylene (10 ml) for 90 minutes. Upon cooling a glass separated which is washed with ether and recrystallised from methanol, affording a white solid (1.31 g), m.p. 122°–123° C.

Compound (F) is prepared analogously from compound (D).

Also prepared are the following prior art compounds:

(H) (Research Disclosure 16444).

(I) (Research Disclosure 16444).

(J) (GB 1.258.924)

Compounds (A) to (E) and comparison compounds (H) and (I) are water-insoluble and are incorporated in the photographic material as solid dispersions as described in Example III.

Compounds (F) and (G) and reference compound (J) are water-soluble and are dissolved in the aqueous gelatino silver halide coating solution as described in Example III.

EXAMPLE III

Preparation of solid dispersion of compound (E)

The following mixture is prepared:
1 g—compound (E)
10 ml—distilled water
0.25 ml—30% anionic wetting agent
50 ml—2 mm glass beads The above ingredients are added to a 100 ml beaker and bead milling is effected by agitating the glass beads with a propeller rotating at 1000 r.p.m. for 24 hours. At the end of this time the glass beads are removed by filtration.

Coatings of the dispersed compound (E) are prepared as follows:

10 ml aliquots of coating solution are made up according the formula:

2 ml solid dispersion (prepared as described above)
0.90 ml silver chlorobromide emulsion (Ag 25 mg/dm$^2$)
0.50 ml 10% gel (decationised blend)
1 ml 1% aqueous formaldehyde solution
0.15 ml 1% anionic wetting agent
0.15 ml 1% nonionic wetting agent
Water to 10 ml.

The anionic wetting agent is an adduct of nonylphenol and 8 moles of ethylene oxide, esterified with sulfuric acid.

The nonionic wetting agent is an adduct of octylphenol and 10 moles of ethylene oxide.

The solution is coated at 40° C. on triacetate base attached to a glass plate, set at 5° C. and dried.

Overall silver coating weight—25 mg/dm$^2$
Overall gel coating weight—80 mg/dm$^2$
Overall compound (E) coating weight—285 mg/dm$^2$ Similar coatings of compounds (A) to (D) and (H) and (I) are also prepared.

The coatings are evaluated as described below:

EXAMPLE IV

All the coatings with compounds (A), (B), (C), (D), (E), (H) and (I) are exposed in an overall manner. The coatings are treated with an activator solution comprising aqueous 2n NaOH for 10 seconds in a bath, washed, fixed in an ammonium thiosulphate (82 g/l) fix for 2 minutes in a bath, washed and then dried. The silver densities obtained by this method for the various coatings are given in Table 1.

TABLE 1

| Compound | D max |
|---|---|
| (A) | 2.04 |
| (B) | 0.96 |
| (C) | 0.98 |
| (D) | 2.03 |
| (E) | >3 |
| (H) | 0.59 |
| (I) | 0.10 |

The results of Table 1 show that the compounds of the present invention are superior to those hitherto known in the insoluble incorporated developer field, and also that it is not possible, with insoluble compounds, to predict a priori the activity of such a compound. Thus compound (I), on electronic argument, should be a more active compound than compound (H), whereas the reverse is true. It is obviously important that the latent solubility of the protected developer in base should be as rapid as possible, and this is achieved in the inventive compounds by the releasable protecting groups being of small bulk, yet rapidly cleaved in the presence of a base.

EXAMPLE V

The water-soluble compounds (F), (G) and (J) are made up according to the following formulation:
200 mg water soluble compounds (F), (G) and (J)
0.90 ml silver chlorobromide emulsion
0.50 ml 10% gel
1 ml 1% aqueous formaldehyde solution
0.15 ml 1% anionic wetting agent according to Example III
0.15 ml 1% nonionic wetting agent according to Example III
Water to 10 ml.

Coatings are made as described in Example IV. The coatings are exposed in an overall manner and processed as described in Example 4 with the following results.

TABLE 2

| Compound | D max after 10 seconds processing time |
|---|---|
| (F) | >3 |
| (G) | >3 |
| (J) | >3 (GB 1258924) |

EXAMPLE VI

Coatings of compounds (A), (B), (C), (D), (E), (H) and (I) are made up as described in Example III, exposed imagewise and processed in an activator solution comprising 2n NaOH for both 5 and 20 seconds. After the appropriate washing, fixing and drying stages the following results are obtained.

TABLE 3

| Compound | 5 seconds activation | | 20 seconds activation | |
|---|---|---|---|---|
| | D min | D max | D min | D max |
| (A) | 0.37 | 1.65 | 0.62 | 2.31 |
| (B) | 0.06 | 0.28 | 0.32 | 1.52 |
| (C) | 0.50 | 1.22 | 0.40 | 1.88 |
| (D) | 0.93 | 1.85 | 1.05 | 2.33 |
| (E) | 0.42 | 2.04 | 0.43 | 2.16 |
| (H) | 0.03 | 0.06 | 0.35 | 1.37 |
| (I) | 0.00 | 0.00 | 0.00 | 0.10 |

The results show the much higher D max values which may be obtained on both short and long processing times by use of the compounds of the present invention. Suppression of D min values by use of antifoggants is available by methods well known so that high D min values are not disadvantageous.

We claim:

1. A substituted hydroquinone compound of the formula $$X \underset{}{\bigcirc} \overset{O}{\underset{\|}{C}} - O - \underset{R^3}{\overset{R^1}{\bigcirc}} \underset{R^4}{\overset{R^2}{}} - O - Y \quad (I)$$

wherein $R^1$, $R^2$, $R^3$ and $R^4$ are each hydrogen, X represents the atoms necessary to complete a 2-, 3- or 4-pyridyl ring quaternized by alkyl or aralkyl sulfate having from 1 to 7 carbon atoms and Y is hydrogen.

2. A compound according to claim 1 wherein $R^1$, $R^2$, $R^3$ and $R^4$ are hydrogen.

3. A compound according to claim 1 wherein Y is hydrogen.

4. A compound according to claim 1 wherein X represents the atoms necessary to complete a 2-, 3- or 4-pyridyl ring quaternised by methyl, ethyl or benzyl sulfate.

5. A compound according to claim 1, wherein $R^1$, $R^2$, $R^3$, $R^4$ and Y are hydrogen and X represents the atoms to complete a 2-, 3- or 4-pyridyl ring quaternised by methyl sulfate.

* * * * *